United States Patent [19]

Strohmeyer et al.

[11] 4,002,539
[45] Jan. 11, 1977

[54] RECOVERY OF CARBOXYLIC ACIDS FROM OXO RESIDUES

[75] Inventors: Max Strohmeyer, Limburgerhof; Werner Hagen, Heidelberg; Heinz Hohenschutz, Mannheim, all of Germany

[73] Assignee: BASF Aktiengesellschaft, Ludwigshafen (Rhine), Germany

[22] Filed: Sept. 23, 1974

[21] Appl. No.: 508,162

[30] Foreign Application Priority Data

Oct. 6, 1973 Germany .......................... 2350313

[52] U.S. Cl. ................................ 203/34; 203/35; 203/71; 203/91; 260/530 R; 260/525
[51] Int. Cl.² ........................................ B01D 3/34
[58] Field of Search ............. 203/34, 35, 91, 71; 260/530 R, 525

[56] References Cited

UNITED STATES PATENTS

| | | | |
|---|---|---|---|
| 2,113,951 | 4/1938 | Shuman | 203/34 |
| 2,255,421 | 9/1941 | Groll et al. | 203/34 X |
| 2,815,355 | 12/1957 | Hill | 260/530 R X |

*Primary Examiner*—James H. Tayman, Jr.
*Attorney, Agent, or Firm*—Johnston, Keil, Thompson & Shurtleff

[57] ABSTRACT

A process for isolating carboxylic acids from residues of the oxo reaction which are obtained as residues, on hydroformylation of ethylene or propylene, optionally after removing a part of the aldehydes produced, subsequent hydrogenation, treatment with aqueous alkali metal hydroxide solutions and subsequent distillation, wherein the residues are acidified with strong mineral acids to a pH of from 2-4, the acidified mixture not containing more than 5 parts by weight of water per part by weight of the carboxylic acids contained in the mixture, the organic phase is then separated off and the carboxylic acids are isolated therefrom by distillation at pressures below 150 mbar. The carboxylic acids obtained can be used as solvents or for the manufacture of esters.

8 Claims, No Drawings

RECOVERY OF CARBOXYLIC ACIDS FROM OXO RESIDUES

The invention is concerned with a process for isolating carboxylic acids from residues of the oxo reaction, which are obtained on hydroformylation of ethylene or propylene, removal of a part of the aldehydes if appropriate, subsequent hydrogenation, treatment with aqueous alkali metal hydroxide solutions and subsequent distillation.

Hydroformylation reaction mixtures contain aldehydes and alcohols and, in addition, small amounts of free carboxylic acids and their esters. The amount of carboxylic acids and esters is increased additionally by treating the crude mixtures with molecular oxygen to remove cobalt. During the conventional hydrogenation of the cobalt-free oxo products or of fractions thereof in the presence of nickel catalysts, the free carboxylic acids and the carboxylic acid esters are virtually not attacked, so that the hydrogenation product contains approximately the same amount of carboxylic acid in the free or esterified form as does the starting product.

In order to be able to work up the hydrogenation products thus obtained in equipment which is not made from alloy steels, and also in order to isolate the portion of the alcohol which is present as esters, the hydrogenation products are treated with sodium hydroxide solution or potassium hydroxide solution prior to being distilled. As a result, the distillation gives residues which contain high-boiling alcohols, glycols and up to 45% by weight of fatty acid salts in addition to some water.

Hitherto, it has only been possible to burn such residues and it has been necessary first to dissolve the fatty acid salts out of the residues by washing with water. Thus, in addition, an aqueous sewage resulted, which had a very high oxygen demand for biological degradation.

Hence, there exists the problem of isolating the utilizable carboxylic acids from the oxo residues and reducing the proportion of sewage having a high biological oxygen demand.

It is the object of the invention to provide a process in which utilizable carboxylic acids are obtained from non-utilizable residues. It is a further object of the invention to provide a process in which the ease of biological degradation of effluents is improved.

In accordance with the invention, these and other objects and advantages are achieved in a process for isolating carboxylic acids from residues of the oxo reaction, which are obtained as residues, on hydroformylation of ethylene or propylene, optionally after removing a part of the aldehydes produced, subsequent hydrogenation, treatment with aqueous alkali metal hydroxide solutions and subsequent distillation, wherein the residues are acidified with strong mineral acids to a pH of from 2 to 4, with the proviso that the acidified mixture does not contain more than 5 parts by weight of water per part by weight of the carboxylic acids contained in the mixture, the organic phase is then separated off and the carboxylic acids are isolated therefrom by distillation at pressures below 150 mbar.

The new process has the advantage that industrially utilizable carboxylic acids are obtained from non-utilizable residues. It has the further advantage that the proportion of sewage having a high biological oxygen demand is greatly reduced.

The new process is noteworthy for the fact that carboxylic acids can be isolated by mere acidification and distillation of the residues.

Residues which are used as starting materials for the present process are obtained in the hydroformylation of ethylene or propylene, especially propylene, with carbon monoxide and hydrogen in the presence of cobalt catalysts, especially cobalt carbonyl and cobalt carbonyl-hydride at temperatures of from 100° to 200° C and at pressures of from 80 to 350 atmospheres. The resulting oxo reaction mixture is as a rule freed from the cobalt by treatment with aqueous acids, preferably in the presence of molecular oxygen. The crude oxo reaction mixture thus obtained, or fractions thereof, after distilling off a part of the aldehydes, is or are hydrogenated directly in the presence of nickel catalysts. The hydrogenated oxo reaction products are treated with aqueous alkali metal hydroxide solutions, especially sodium hydroxide solution, in order to neutralize the carboxylic acids contained therein and to saponify the carboxylic acid esters. The alkanols are distilled from the mixture thus obtained. The residue obtained is a mixture which contains high-boiling alcohols, alkali metal salts of fatty acids and a little water. Of course propionic acid is the acid to be isolated from the residues of the hydroformylation of ethylene whilst butyric acids are the acids to be isolated from the residues of the hydroformylation of propylene. A typical mixture of an oxo-$C_4$ residue contains, for example, from 25 to 43% by weight of sodium butyrate, approx. 2% by weight of sodium formate, from 25 to 45% by weight of organic high-boiling solvents (alkanols and glycols) and from 20 to 35% by weight of water.

The residues thus obtained are acidified with strong mineral acids. Examples of suitable acids are hydrochloric acid and sulfuric acid. The choice of the acid depends on whether the acids are present in the residue as the sodium salt or as the potassium salt. The objective is to produce an alkali metal salt with strong mineral acids which is as readily soluble in water as possible. The amount of the strong mineral acid added is such that the mixture has a pH of from 2 to 4, especially from 2 to 3. Furthermore, it is necessary to ensure that the acidified mixture contains not more than 5 parts by weight of water per part by weight of carboxylic acid contained in the mixture.

The mixture which has been acidified in this way separates into phases. The organic phase is separated off and the carboxylic acids are isolated therefrom by distillation at pressures below 150 mbar. This process can be carried out batchwise, for which columns with from 40 to 60 theoretical plates, and a pressure of from 10 to 50 mbar, are used with advantage. The overhead obtained consists of carboxylic acids which are 99% pure. However, since it is advantageous to employ the shortest possible residence times during distillation, the carboxylic acids are preferably first subjected to crude distillation in a column with from 10 to 30 theoretical plates and a pressure of from 10 to 150 mbar, and the carboxylic acids thus obtained, which are still contaminated, are purified in a second column which advantageously has from 40 to 70 theoretical plates.

Propionic acid and butyric acid obtained according to the process of the invention can be used as gelling auxiliaries or for the manufacture of esters which are used as solvents.

The Examples which follow are intended to illustrate the process of the invention.

EXAMPLE 1

An alcohol mixture obtained by hydrogenation of hydroformylation products of propylene which — based on the anhydrous product — contains 85% of n- and i-butanol, 11% of high-boiling oxygen-containing substances, 1.8% of free butyric acid and 2.2% of butyric acid esters is heated, after addition of 25 percent strength sodium hydroxide solution, to 170° C in a flow tube at 10 atmospheres gauge; the amount of sodium hydroxide solution added is so chosen that the reaction product still contains 0.1% of unconsumed sodium hydroxide solution. Thereafter, the bulk of the butanols is distilled continuously from the neutralized and saponified alcohol mixture in a 1st column. The residue obtained at the bottom, which still contains 40% of butanols, is passed into a 2nd column in which the residual amount of butanol is driven off as a water azeotrope by means of steam. The residue collecting at the bottom of this column has the following average composition:

| | |
|---|---|
| Sodium butyrate | 36.3% |
| Sodium formate | 1.6% |
| NaOH | 0.1% |
| High-boilers | 42.0% |
| Water | 20.0% |

The residue, which is at 110°, is withdrawn in a continuous stream from the lower end of the column by means of an automatic level controller, mixed with 0.29 part of condensation water per part by weight of residue and cooled to 35° C.

The cooled product is charged into a stirred kettle where it is continuously acidified to pH 2.3 with 40 percent strength waste sulfuric acid, whilst stirring vigorously. The requisite amount of sulfuric acid, which in the case of the composition of the residue shown above amounts to 0.34 part per part of residue-containing condensate is controlled automatically, to compensate for fluctuations in the composition, by a measuring electrode, set to pH 2.3 and immersed in the reaction mixture — via a regulating valve. The mixture contains 2.6 parts by weight of water per part by weight of carboxylic acids.

The two-phase emulsified mixture formed in the reaction is withdrawn continuously through an overflow and charged into a heated separator in which it splits into two separate phases:

1. An organic upper phase, comprising 45% by weight of the total amount and consisting of the high-boiling alcohols contained in the distillation residue, 36.7% of butyric acids and 9.9% of water, and
2. An aqueous phase corresponding to 35% by weight of the total amount, which consists of a 27 percent strength aqueous sodium sulfate solution in which the only organic products present are 0.4% of butyric acids, 0.8% of formic acid and 0.5% of alcoholic substances.

The organic phase, which contains 99% of the amounts of butyric acid present in the distillation residue, is worked up as follows to give pure butyric acid.

The mixture obtained, which consists of 53.4% of high-boiling alcohols, 36.7% of n- and i-butyric acid and 9.9% of water, is separated continuously, in a corrosion-resistant packed column of 7.5 m height and 0.5 diameter, which is filled with 40 × 40 mm Pall rings and fitted with a circulatory vaporizer, into a butyric acid concentrate of low alcohol content, which passes overhead, and a residue which is almost free of butyric acid.

The feedstock is preheated to from 135° – 137° C in a preheater and introduced into the column through a lateral inlet 1 m from the bottom end of the column, at a rate of 1.2 m³/hour. A reflux ratio of about 1:1 is set up in the upper part of the column by recycling a part of the distillate into the top of the column. Using an average column pressure of 60 mbar, a bottoms temperature of 145°–148° C and a top temperature of 76°–82° C, approximately equal amounts of distillate and residue are obtained, having the following contents of butyric acid and of water:

| | % Butyric acid | % Water |
|---|---|---|
| Distillate | 70.0 | 18.5 |
| Residue | 2.4 | — |

It can be seen from these figures that about 96% of the butyric acid present in the starting product have accumulated in the distillate and that the amount of butyric acid esterified is less than 1%. The analytical data of the distillate further show that a small amount of the alcohols also distils over when topping the butyric acid.

The butyric acid concentrate obtained on topping is subsequently worked up batchwise in a still with a column having 70 bubble plates, to give pure n-butyric acid and i-butyric acid.

EXAMPLE 2

The separation process described in Example 1 is repeated, with the modification that the stirred kettle which serves as the decomposition position vessel is additionally fed, per part of residue containing butyric acid, with 0.56 part of a further distillation residue, containing alkali metal salt, which is obtained on analogously working up a hydrogenation product which has been obtained from ethylene hydroformylation products and saponified with potassium hydroxide solution, and which contains 48.7% of potassium propionate, 34.4% of higher alcohols and 16.9% of water.

The temperature at which the two residues are run in is adjusted so that the temperature in the stirred kettle rises to from 50° to 60° C as a result of the heat of reaction which is liberated.

The decomposition agent used is 38 percent strength waste hydrochloric acid, the addition of which is regulated automatically, as in Example 1, by a measuring electrode set to pH 2.3 and immersed in the reaction mixture. The total water content of the material in the stirred kettle is raised to 2.2 parts per part of total carboxylic acid by introducing 0.38 part of water of condensation per part of residue containing butyric acid.

After the phase separation, 100 parts of reaction mixture give:

a. 46 parts of an upper layer containing 91.2% of organic substances, of which 24.3% are butyric acid and 12.3% propionic acid in the free form, and b. 54 parts of an aqueous lower layer having a residual butyric acid content of 0.9% and propionic acid content of 2.7%.

The butyric acid content of the upper phase corresponds to the separation of 96% of the butyric acid, whilst only 80% of the propionic acid are separated off in the upper phase.

The organic phase is worked up in accordance with the two-stage process described in Example 2. However, only the n-butyric acid and a part of the i-butyric acid can be obtained in satisfactory yield and purity. The fraction containing the remainder of the i-butyric acid and the propionic acid is burnt together with the distillation residues.

The aqueous phase is fed to a biological treatment plant to remove the organic impurities.

We claim:

1. A process for isolating a carboxylic acid selected from the group consisting of propionic acid and butyric acid from the residue which is obtained in the production of propanol or butanol by the catalytic hydroformylation of ethylene or propylene, subsequent hydrogenation of the resulting crude propionaldehyde or butyraldehyde, treatment of the hydrogenated product mixture with an aqueous alkali metal hydroxide solution in order to saponify propyl propionate or butyl butyrate formed as a byproduct and distilling off the propanol or butanol product, said residue consisting essentially of high-boiling alcohols, water and alkali metal propionate or butyrate, which process comprises:

acidifying said residue with a strong mineral acid selected from the group consisting of sulfuric acid and hydrochloric acid to form the corresponding alkali metal sulfate or chloride, the amount of acid being sufficient to yield a mixture with a pH of from 2 to 4 with the proviso that the resulting acidified mixture does not contain more than 5 parts by weight of water per part by weight of the propionic or butyric acid;

separating the organic phase thus obtained from the aqueous phase; and isolating propionic or butyric acid by distillation from the organic phase.

2. A process as claimed in claim 1, wherein an oxo-$C_4$ residue mixture is used which contains from 25 to 43% by weight of sodium butyrate, approx. 2% by weight of sodium formate, from 25 to 45% by weight of organic high-boilers and from 20 to 35% by weight of water.

3. A process as claimed in claim 1, wherein the mixture is acidified to a pH of from 2 to 3.

4. A process as claimed in claim 1, wherein, after separating off the aqueous phase, the crude carboxylic acids are distilled from the organic phase in a first column, using a short residence time, and are purified by distillation in a second column.

5. A process as claimed in claim 1 wherein the acid being isolated is butyric acid.

6. A process as claimed in claim 1 wherein the acid being isolated is propionic acid.

7. A process as claimed in claim 1 wherein the acid being isolated is a mixture of propionic and butyric acid.

8. A process as claimed in claim 1 wherein the distillation of the acid is carried out at a pressure below about 150 mbar.

* * * * *